(12) United States Patent
Bruecker et al.

(10) Patent No.: US 7,905,883 B2
(45) Date of Patent: Mar. 15, 2011

(54) LOCKING TRIPLE PELVIC OSTEOTOMY PLATE AND METHOD OF USE

(75) Inventors: Kenneth Bruecker, Ventura, CA (US);
Alex Khowaylo, Waldwick, NJ (US);
Michael Khowaylo, Mahwah, NJ (US);
Gary Thau, Morgantown, PA (US);
Robert Young, Loganville, GA (US);
Patrick White, West Chester, PA (US)

(73) Assignee: Greatbatch Medical S.A., Orvin (CH)

( * ) Notice: Subject to any disclaimer, the term of this patent is extended or adjusted under 35 U.S.C. 154(b) by 757 days.

(21) Appl. No.: 11/930,242

(22) Filed: Oct. 31, 2007

(65) Prior Publication Data

US 2008/0082102 A1    Apr. 3, 2008

Related U.S. Application Data

(63) Continuation-in-part of application No. 10/809,034, filed on Mar. 25, 2004, now Pat. No. 7,722,653.

(60) Provisional application No. 60/457,786, filed on Mar. 26, 2003.

(51) Int. Cl.
*A61B 17/56* (2006.01)

(52) U.S. Cl. .......................................... 606/70; 606/291

(58) Field of Classification Search .................... 606/70, 606/291
See application file for complete search history.

(56) References Cited

U.S. PATENT DOCUMENTS

| | | | |
|---|---|---|---|
| 643,773 A | 2/1900 | Metcalf | |
| 2,699,774 A | 1/1955 | Livingston | |
| 3,463,148 A * | 8/1969 | Treace | 606/286 |
| 3,552,389 A | 1/1971 | Allgover et al. | |
| 3,659,595 A | 5/1972 | Haboush | |
| 3,716,050 A | 2/1973 | Johnston | |
| 3,824,995 A | 7/1974 | Getscher et al. | |
| 3,842,825 A | 10/1974 | Wagner | |
| 4,120,298 A | 10/1978 | Fixel | |
| 4,219,015 A | 8/1980 | Steinemann | |
| 4,403,606 A | 9/1983 | Woo et al. | |
| 4,408,601 A | 10/1983 | Wenk | |
| 4,409,973 A | 10/1983 | Neufeld | |
| 4,421,112 A | 12/1983 | Mains et al. | |
| 4,454,876 A | 6/1984 | Mears | |
| 4,493,317 A | 1/1985 | Klaue | |
| 4,498,601 A | 2/1985 | Fort | |

(Continued)

FOREIGN PATENT DOCUMENTS

DE    0207884    3/1909

(Continued)

OTHER PUBLICATIONS

AXIS Fixation System by Sofamor Danek, Jun. 2008.

(Continued)

*Primary Examiner* — Eduardo C Robert
*Assistant Examiner* — David W Bates
(74) *Attorney, Agent, or Firm* — Michael F. Scalise

(57) ABSTRACT

A TPO bone plate with an offset longitudinal axis has a bone-contacting bottom side and a top side. Sets of overlapping holes communicate through the plate from the top to the bottom side. The overlapping holes have multifaceted surfaces such as a threaded surface or a coaxial series of annular grooves. The sets of overlapping holes are adapted to receive a bone screw with a head and a bone-engaging thread.

25 Claims, 5 Drawing Sheets

U.S. PATENT DOCUMENTS

| | | | |
|---|---|---|---|
| 4,501,268 A | 2/1985 | Comparetto | |
| 4,502,474 A | 3/1985 | Comparetto | |
| 4,509,511 A | 4/1985 | Neufeld | |
| 4,513,744 A | 4/1985 | Klaue | |
| 4,545,876 A | 10/1985 | McGivern, Jr. | |
| 4,565,191 A | 1/1986 | Slocum | |
| 4,565,193 A | 1/1986 | Streli | |
| 4,611,581 A | 9/1986 | Steffee | |
| 4,662,891 A | 5/1987 | Noiles | |
| 4,677,973 A | 7/1987 | Slocum | |
| 4,696,290 A | 9/1987 | Steffee | |
| 4,762,122 A | 8/1988 | Slocum | |
| 4,790,297 A | 12/1988 | Luque | |
| 4,794,918 A | 1/1989 | Wolter | |
| 4,800,874 A | 1/1989 | David et al. | |
| 4,867,144 A | 9/1989 | Karas et al. | |
| 4,875,475 A | 10/1989 | Comte et al. | |
| 4,957,479 A | 9/1990 | Roemer | |
| 4,957,496 A | 9/1990 | Schmidt | |
| 4,957,497 A | 9/1990 | Hoogland et al. | |
| 4,959,065 A | 9/1990 | Arnett et al. | |
| 4,988,350 A | 1/1991 | Herzberg | |
| 5,002,544 A | 3/1991 | Klaue et al. | |
| 5,006,120 A | 4/1991 | Carter | |
| 5,015,248 A | 5/1991 | Burstein et al. | |
| 5,085,660 A | 2/1992 | Lin | |
| 5,087,260 A | 2/1992 | Fixel | |
| 5,176,679 A | 1/1993 | Lin | |
| 5,216,941 A | 6/1993 | Kolvereid | |
| 5,232,249 A | 8/1993 | Kolvereid | |
| 5,261,910 A | 11/1993 | Warden et al. | |
| 5,275,601 A | 1/1994 | Gogolewski et al. | |
| 5,304,180 A | 4/1994 | Slocum | |
| 5,324,290 A | 6/1994 | Zdeblick et al. | |
| 5,364,399 A | 11/1994 | Lowery et al. | |
| 5,601,553 A | 2/1997 | Trebing et al. | |
| 5,681,311 A | 10/1997 | Foley et al. | |
| 5,709,686 A | 1/1998 | Talos et al. | |
| 5,733,287 A | 3/1998 | Tepic et al. | |
| 5,741,258 A | 4/1998 | Klaue et al. | |
| 5,810,823 A | 9/1998 | Klaue et al. | |
| 5,851,207 A * | 12/1998 | Cesarone | 606/86 B |
| 5,904,684 A | 5/1999 | Rooks | |
| 5,968,047 A | 10/1999 | Reed | |
| 5,976,141 A | 11/1999 | Haag et al. | |
| 5,997,541 A | 12/1999 | Schenk | |
| 6,022,350 A * | 2/2000 | Ganem | 606/272 |
| 6,048,344 A | 4/2000 | Schenk | |
| 6,096,060 A | 8/2000 | Fitts et al. | |
| 6,206,881 B1 | 3/2001 | Frigg et al. | |
| 6,309,393 B1 | 10/2001 | Tepic et al. | |
| 6,322,562 B1 | 11/2001 | Wolter | |
| 6,331,179 B1 | 12/2001 | Freid et al. | |
| 6,358,250 B1 | 3/2002 | Orbay | |
| 6,406,478 B1 | 6/2002 | Kuo | |
| 6,623,486 B1 | 9/2003 | Weaver et al. | |
| 6,669,701 B2 * | 12/2003 | Steiner et al. | 606/282 |
| 6,706,046 B2 | 3/2004 | Orbay et al. | |
| 6,719,759 B2 | 4/2004 | Wagner et al. | |
| 6,821,278 B2 | 11/2004 | Frigg et al. | |
| 7,063,701 B2 | 6/2006 | Michelson | |
| 7,090,676 B2 | 8/2006 | Huebner et al. | |
| 7,695,472 B2 | 4/2010 | Young | |
| 2002/0045901 A1 | 4/2002 | Wagner et al. | |
| 2002/0156474 A1 | 10/2002 | Wack et al. | |
| 2002/0183752 A1 | 12/2002 | Steiner et al. | |
| 2003/0040748 A1 | 2/2003 | Aikins et al. | |
| 2004/0167522 A1 | 8/2004 | Niederberger et al. | |
| 2004/0181228 A1 | 9/2004 | Wagner et al. | |
| 2005/0216008 A1 | 9/2005 | Zwirnmann et al. | |
| 2005/0216009 A1 | 9/2005 | Michelson | |
| 2006/0212035 A1 | 9/2006 | Wotton, III | |
| 2008/0039851 A1 * | 2/2008 | Schulz et al. | 606/87 |

FOREIGN PATENT DOCUMENTS

| | | |
|---|---|---|
| DE | 2806414 | 10/1978 |
| DE | 4341980 | 6/1995 |
| DE | 4343117 | 6/1995 |
| EP | 0100114 | 2/1984 |
| EP | 0355035 | 2/1990 |
| FR | 2472373 | 7/1981 |
| FR | 2556583 | 6/1985 |
| FR | 2606268 | 5/1988 |
| WO | 0053110 | 9/2000 |
| WO | 0053111 | 9/2000 |
| WO | 0119267 | 3/2001 |
| WO | 0154601 | 8/2001 |
| WO | 0157834 | 8/2001 |
| WO | 0200127 | 1/2002 |
| WO | 02096309 | 12/2002 |
| WO | 2004089233 | 10/2004 |
| WO | 2005117732 | 12/2005 |

OTHER PUBLICATIONS

The Canine Pelvis and the Pelvic Limb by Barclay Slocum and Theresa Devine Slocum, Appendix A.

Brueckmann et al., Proximal Tibial Osteotomy, Orthopedic Clinics of North America, vol. 13, No. 1, (Jan. 1982), p. 3-16.

Sundaram et al., Dome Ostotomy of the Tibia for Osteoarthritis of the Knee, The Journal of Bone and Joint Surgery, vol. 68-B, No. 5, (Nov. 1986), p. 782-786.

Slocum et al., Tibial Plateau Leveling Osteotomy for Repair of Cranial Cruciate Ligament Rupture in the Canine Veterinary Clinics of North America: Small Animal Practice, vol. 23, No. 4, (Jul. 1993), p. 777-795.

Reif et al., Effect of Tibial Plateau Leveling on Stability of the Canine Cranial Cruciate-Deficient Stifle Joint: An In Vitro Study, Veterinary Surgery, 31, (2002), p. 147-154.

Wheeler et al., In Vitro Effects of Osteotomy Angle and Osteotomy Reduction on Tibial Angulation and Rotation During the Tribal Plateau-Leveling Osteotomy Procedure, Veterinary Surgery, 32, (2003), p. 371-377.

Fettig et al., Observer Variability of Tibial Plateau Slope Measurement in 40 Dogs With Cranial Cruciate Ligament-Deficient Stifle Joints, Veterinary Surgery, 32, (2003), p. 471-478.

Miniaci et al., Proximal Tibial Osteotomy. A New Fixation Device, PubMed Article.

Lang et al., Cylindrical Osteotomy of the Upper End of the Tibia, PubMed Article.

Schneider et al., Cylindrical Osteotomy of the Upper Extremity of the Tibia with Advancement of the Patellar Ligament. Biomechanical Treatment of Gonarthrosis, PubMed Article.

Cassarino et al., High Domed Tibial Osteotomy in the Treatment of Angular Deviations of the Knee. A New System of Surgical Instrumentation, PubMed Article.

Soccetti et al., Domed High Tibial Osteotomy: The Long-Term Results in Tibiofemoral Arthritis with and without Malalignment of the Extensor Apparatus, PubMed Article.

Slocum et al., Current Techniques in Small Animal Surgery, Baltimore: Williams & Wilkins, TX-4-606-643, (1997), 1340 pages.

Sundaram et al., Dome osteotomy of the tibia for osteoarthritis of the knee, PubMed Article.

International Search Report, PCT1B2004/001784.

* cited by examiner

LOCKING TRIPLE PELVIC OSTEOTOMY PLATE AND METHOD OF USE

CROSS REFERENCE TO RELATED APPLICATIONS

This application is a continuation-in-part application of prior U.S. patent application Ser. No. 10/809,034, filed on Mar. 25, 2004, now U.S. Pat. No. 7,722,653 which claims priority from U.S. provisional patent application Ser. No. 60/457,786, filed Mar. 26, 2003, the contents of which are incorporated herein by reference thereto and relied upon.

BACKGROUND OF THE INVENTION

This invention relates to devices, implants and prostheses used in orthopedic surgery, and, more particularly, to bone plates used in Triple Pelvic Osteotomy (TPO), to join reformed bone and thus promote healing.

Bone plates have been used to repair fractured or opened bones at least since the time of the Incas. The innovations in this field have involved plate materials, plate form, and the means of fixing the plate across the bone fragments to be joined.

In an effort to deal with the fixation of a bone plate, a compressive screw system, also known as the DCS bone plate system, was developed and in use in trauma surgery for many years. The procedures for use of this system are well documented by the AO Institute, an institute having as one of its goals, the promotion of new orthopedic surgical procedures. This system included a bone plate having slots communicating there through. A land in which the slot is wider at one end defines a stepped surface adjacent the portion of the slot that extends through the bone plate. The stepped surface is generally cut with a spherical endmill, thus creating a spherical stepped surface.

In a still further development, bone plates have been developed having individual threaded apertures and non-threaded apertures interspersed along the length of the plate. In this and other designs, the distance between holes has become a standard. Although an improvement over the inserts noted above, the locking positions are pre-defined, and only available in limited locations, which also reduce surgical flexibility.

In yet another solution, PCT application no. WO01/54601 combines the features of the DCS system discussed above with a locking screw. This design combines the features of the DCS system with a locking screw. Such a system is known as the combi-slot. In this design, the stepped surface of the slot is generally ramped or tapered so as to be deeper at one end than at another. This enables the positioning and selective fixing of the bone plate for compressing two bone fragments together with a preload created by wedging action. In this manner, the bones are placed in a position that the surgeon believes would best promote healing.

While patent application no. WO01/54601 has proven advantageous because screws can be locked to the plate, the presence of an unthreaded slot limits the users ability to have multiple orientations for the screw.

In a further development, the AO Institute has studied and proposed the use of endpegs which are rigidly fixed in the extreme ends of the bone plate. Such an arrangement has been shown to better resist the flexing of the bone than use of a bone screw alone. Flexing can otherwise loosen the connection between the bone plate and bone in other bone plate systems.

In another development, German patent DE 4341980 A1, published on Jun. 14, 1995, describes a bone plate 2 having an elongated slot 8 in which the sidewalls of the long sides of the slot are not parallel and are further provided with an internal thread 9. Corresponding bone screws 3 or inserts 6 have a head 5 with an external taper 4 and thus can be fixed into any point along the length, but to various depths of penetration. Therefore, the final configuration upon fixing is indeterminate and, due to the small amount of contact between the threads of the insert or screw and the slot, as well as the fact that the screw will be able to slide in one direction, the design does not appear to lend itself to reliable fixing.

U.S. Pat. No. 5,324,290 shows a complex hone plate having slots with countersunk circular recessed cut at intervals along the slot (a similar arrangement is shown in U.S. Pat. No. 4,696,290). It further shows the bone plate torqued against the bone so as to at least marginally conform to the shape of the bone (see FIG. 2). Other patents of interest include U.S. Pat. Nos. 3,716,050, 3,659,595, 5,681,311, 5,261,910, and 5,364,399, all showing combinations of conventional slots and recesses which do not fully accommodate a bone screw having a threaded head.

In a Triple Pelvic Osteotomy, it is necessary to treat a subluxed hip in a canine, which is a genetic abnormality. This is when the femoral head is not sufficiently covered (less than 50% coverage) by the rim of the acetabulum (see pg. 472 of Appendix A attached and incorporated herein by reference thereto).

Consequently, a TPO plate is made up essentially of two plates that are non-parallel to each other, being rotated with respect to each other about an axis, and fixed together by an offset web. Different cases necessitate different angular changes to best cover the femoral head. If a femoral head is covered 30 degrees instead of 50, for example, one would need to use a 20 degree TPO plate to reach 50% coverage, and so on. The plate positions the bone at the correct anatomical angle.

In another product variation, expandable, lockable inserts enter into the slots of a standard bone plate. When the bone screw passes through one of these inserts and is torqued down, the insert expands and locks the screw in place. However, this insert is locked in a secondary operation. This is not desirable because this requires more operating room time and adds complexity to the procedure. Further, the inserts must be added in the specific location before the plate is fixed to the bone and cannot be subsequently inserted. This limits the choice of placement during surgery if the need arises.

Also, the above insert design relies on a friction lock via contact between two surfaces. Friction locks are not reliable and come lose more easily than threaded locked holes. The result of such a design is inferior to that of the threaded plate and screw designs discussed below.

In prior art TPO plates, it is known that the bone screws can come lose, causing pain and/or requiring corrective surgery. What is needed, therefore, is a TPO plate which can be firmly fixed to the bone in a manner to minimize the likelihood of loosening of the bone screws. In addition, what is needed is a TPO plate where the holes are located to achieve the best anatomical location of the screws in the bone.

What is needed is a bone plate that provides the surgeon with multiple orientations for the locking screw and thus, plate placement, while reliably and permanently fixing the bone plate to the bone fragments in any hole position. More specifically, what is needed is a bone plate that provides this choice of plate placement while reliably and permanently fixing the bone plate to the bone fragments, in any hole position.

What is needed is a bone plate with holes that create at least unidirectional compression.

SUMMARY OF THE INVENTION

A TPO bone plate is provided having an offset longitudinal axis, a bone-contacting bottom side and a top side. Sets of overlapping holes communicate through the plate from the top to the bottom side. The overlapping holes have multifaceted surfaces such as a threaded surface or a coaxial series of annular grooves. The sets of overlapping holes are adapted to receive a bone screw with a head and a bone-engaging thread.

An object of the invention is to provide an orthopedic surgeon greater flexibility of choice in that a threaded peg providing secure fixing can be positioned at any interval along the bone plate, including at its extreme ends.

DETAILED DESCRIPTION OF THE PREFERRED EMBODIMENT

Figure 1:
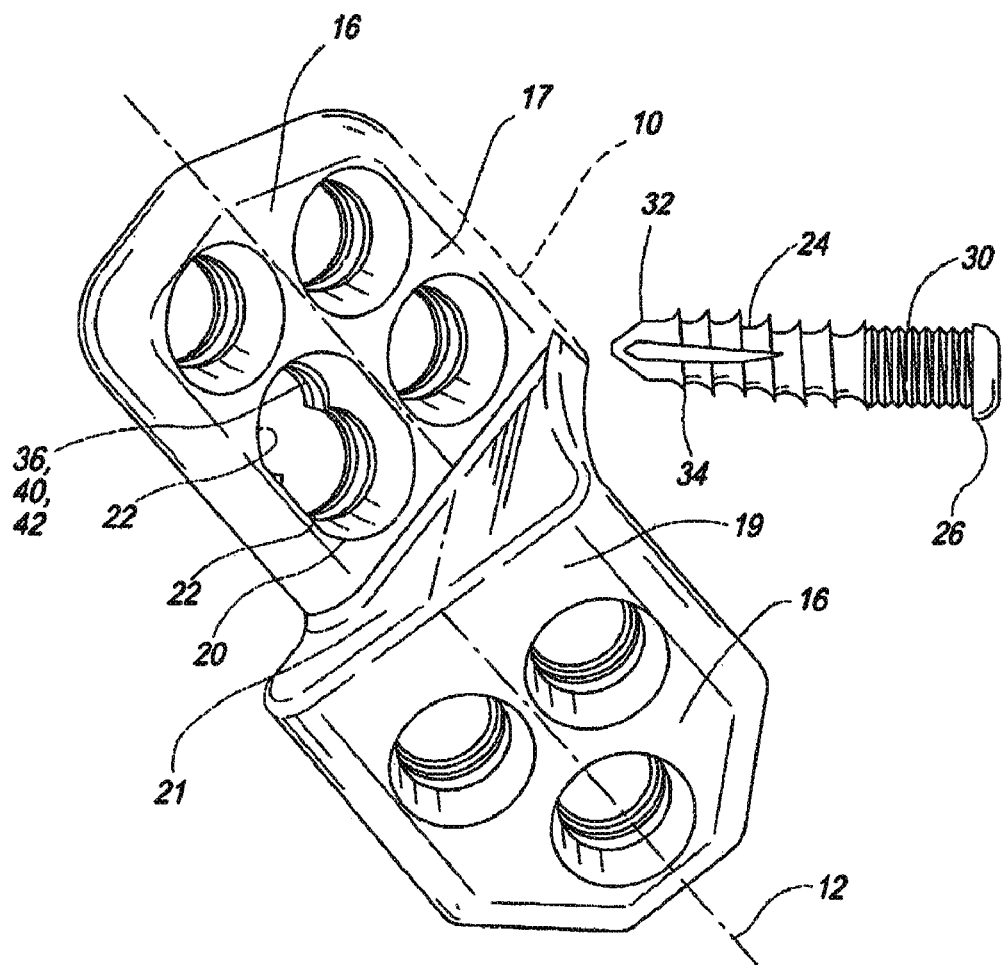
FIG. 1 is a perspective view of the bone plate of the invention.
Figure 2:
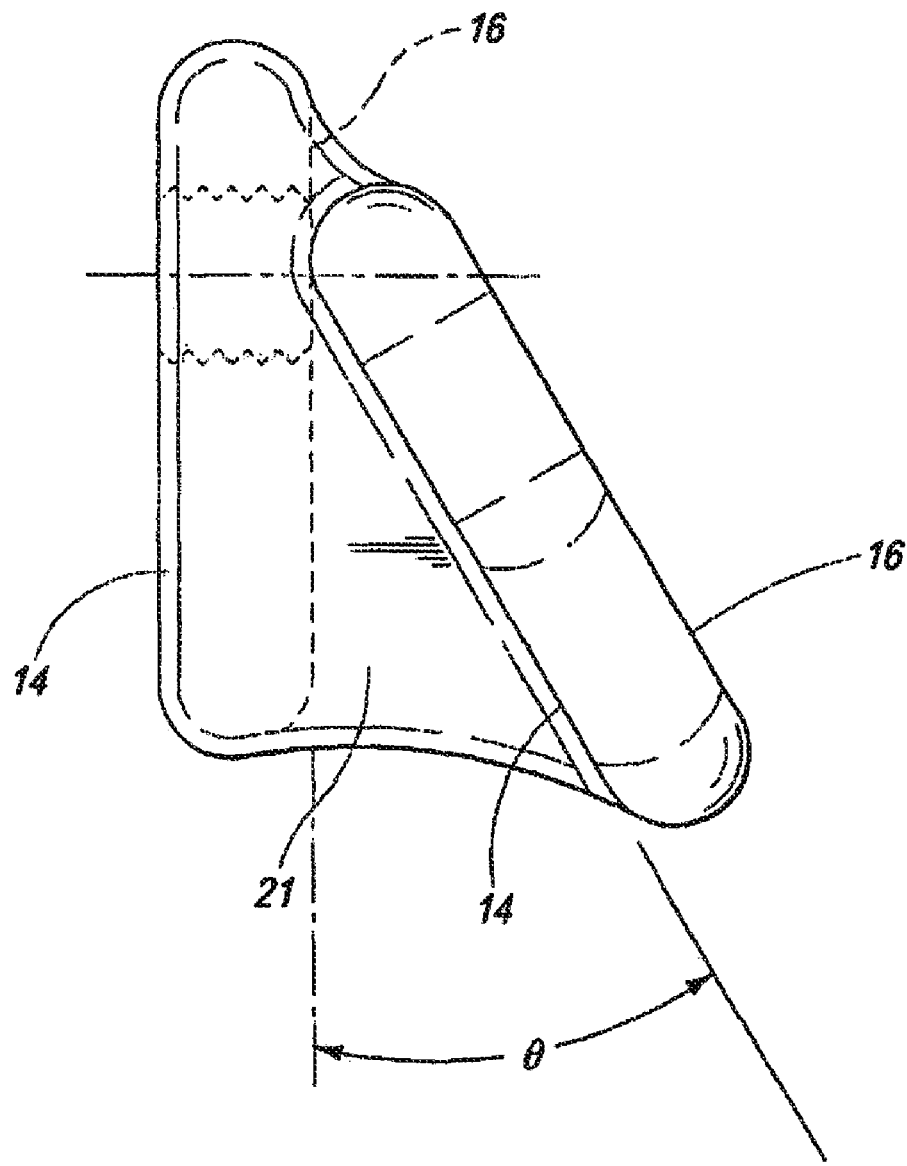
FIG. 2 is a side view of the bone plate of FIG. 1.
Figure 3:
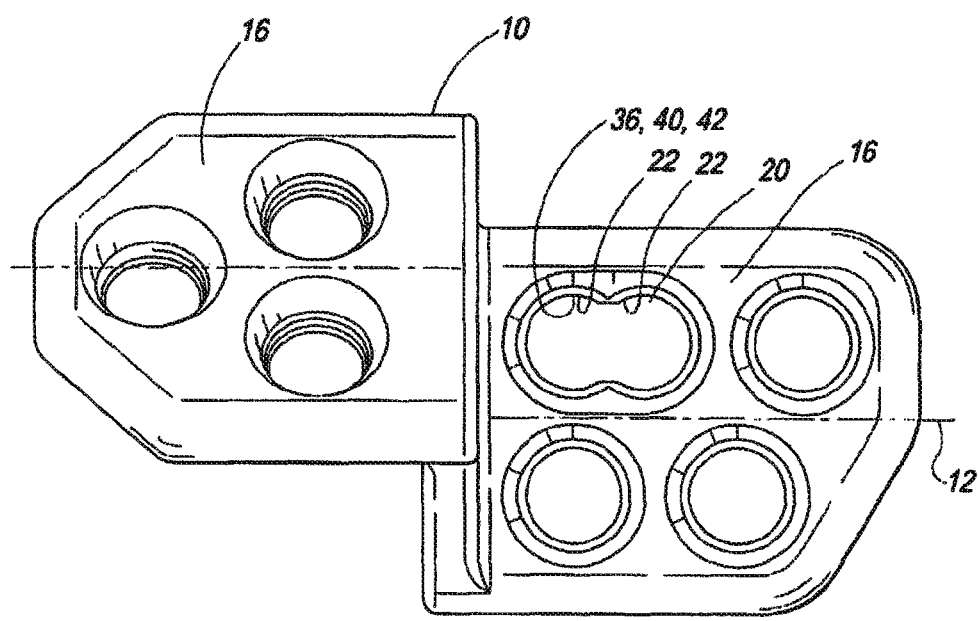
FIG. 3 is a front view of the bone plate of FIG. 1.

Referring now to FIGS. 1 to 3, a bone plate 10 with an offset longitudinal axis 12 has a bone-contacting bottom side 14 and a top side 16 comprised in two flanges 17 and 19 that are non-parallel to each other, being rotated with respect to each other about an axis by an amount θ, and fixed together by an offset web 21.

Sets 20 of overlapping holes 22 communicate through the plate 10 from the top side 16 to the bottom side 14. The overlapping holes 22 are adapted to receive a bone screw 24 with a head 26 having a thread 30 and, on an opposite end 32, a body having a bone-engaging thread 34.

The Sets 20 of overlapping holes 22 allow for further adjustability and flexibility in positioning of the bone plate 10 during surgery. The overlapping holes 22 are formed normal to the top side 16 of the plate 10.

The overlapping holes 22 have multifaceted surfaces 36. In one embodiment, the multifaceted surface 36 is a threaded surface 40. In another embodiment, the multi-faceted surface 36 is a coaxial series of annular grooves 42.

Overlapping holes 22 are formed individually at an angle Ø offset from normal to the top side 16 of the plate 10. Such allows further flexibility of choice to the surgeon as to where and how to fasten the bone plate 10. Where these overlapping holes 22 are oriented perpendicularly to the top side 16 of the bone plate 10, he may chose to fasten the plates in a conventional manner, namely, perpendicular to the top side of the plate.

Because of the organic form of bones in canines, no two bones are identical. In fact among canines with hip abnormalities, variations from the norm can be very significant. Consequently, bone plates 10 must be provided to accommodate different angular changes in order to best cover the femoral head. If a femoral head is covered 30 degrees instead of 50, for example, one would need to use a 20 degree TPO plate to reach 50% coverage, and so on. The TPO bone plate 10, therefore, positions the bone at the correct anatomical angle.

In a preferred embodiment, some of the overlapping holes 22 are formed normal to the top side 16 of the plate 10.

Figure 4:
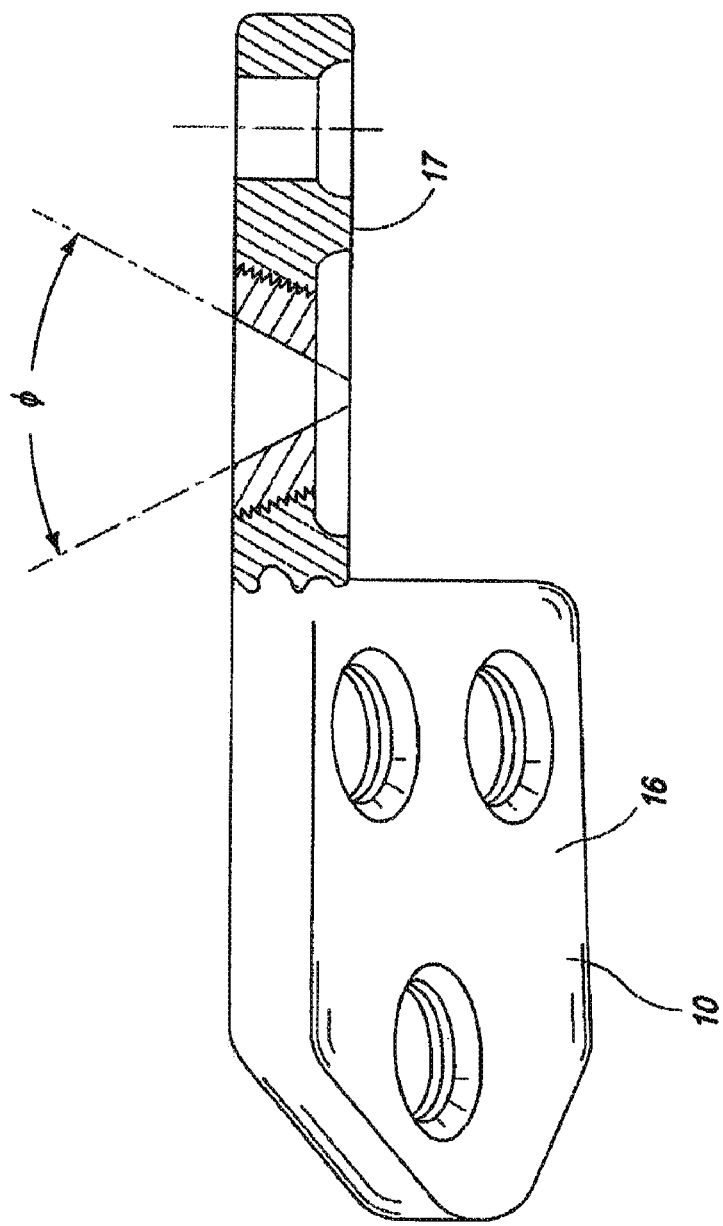
FIG. 4 is a top view of the bone plate of the invention

Referring now to FIG. 4, alternatively, some or all of the overlapping holes 22 may be formed at an angle Ø offset from normal to the top side 16 of the plate 10.

In an alternate embodiment, the bone plate 10 may include sets 20 of three overlapping holes 22 (not shown). Where these overlapping holes 22 are oriented perpendicularly to the top side 16 of the bone plate 10, the surgeon may chose to fasten the plates in a conventional manner.

Figure 5:
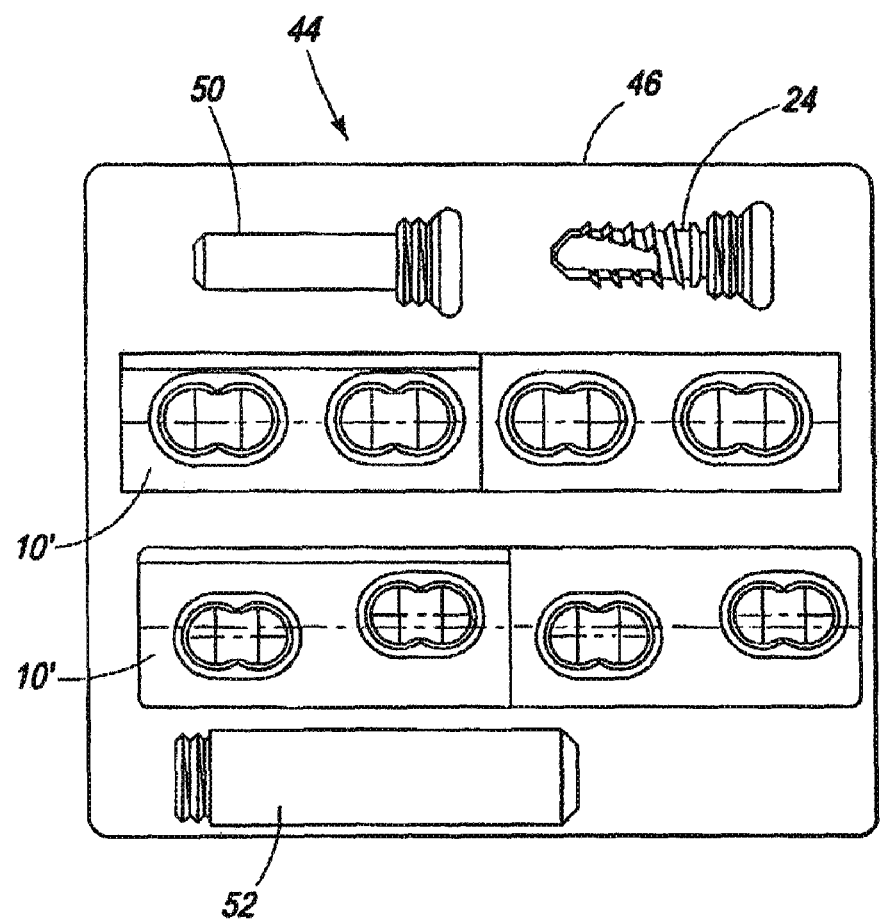
FIG. 5 is a top view of a kit of the invention.
FIGs in Appendix A include figures that illustrate the use of the bone plate of FIG. 1.

Referring now to FIG. 5, in another embodiment, orthopedic kits 44 are provided which include a case 46, a bone plate 10', a variety of bone screws 24, threaded pegs 50 of various lengths, and a drill guide 52. The drill guide 52 has a threaded end 54 that threads into the thread 40 of an overlapping hole 22. The drill guide 52 has a main drill guide surface 56 to securely hold the drill guide in a desired orientation with respect to the bone plate 10 in order to stabilize a drill (not shown) used in an orthopedic procedure.

Note that the threaded apertures 100 used in the invention provide hole centers located at specific locations (as opposed to apertures that are formed as a slot). Use of threads centered at a specific point allows the bone screw to be fixed at a specific location at which the surgeon may judge the bone structure to be best suited to support such a bone screw. Unlike designs using a slot, the apertures 100 of the invention eliminate wander of the screw in the aperture. This further permits placement at specific locations for buttressing and/or secure fixing in neutral screw loading areas.

In a preferred embodiment, the bone plate 10 includes overlapping threaded holes 22 on one side of the web 21, thereby providing the ability to the surgeon of unidirectionally compressing one bone fragment against the other.

In an alternate embodiment, shown in FIG. 4, the bone plate 10' includes overlapping threaded holes 22 on opposite sides of the web 21. This enables bi-directional compression of the bone fragments against each other to ensure more rapid healing.

A detailed description of the method of use of the bone plate 10 is attached as Appendix A, and incorporated herein by reference thereto.

In an advantage, the bone plate 10 provides greater flexibility of choice by providing multiple overlapping holes 22 oriented so as to maximize the surgeon's flexibility of placement of the plate.

In another advantage, the bone plate 10 uses locking screws which interface with corresponding threaded locking holes to better ensure secure fixing of the plate to the bone.

In still another advantage, the threaded apertures 40 of the bone plate 10 are provided with threads cut perpendicular to the top side 16 of the bone plate, as well as at an angle Ø to normal.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A bone plate, comprising:
   a) a first flange lying in a first plane, the first flange having a first thickness extending from a top first flange surface to a bottom first flange surface with at least one threaded hole formed through the first thickness, wherein the first flange has a first longitudinal axis;
   b) a second flange lying in a second plane, the second flange having a second. thickness extending from a top second flange surface to a bottom second flange surface with at least one threaded hole formed through the second thickness, wherein the second flange has a second longitudinal axis;
   c) a web connecting the first flange lying in the first plane to the second flange lying in the second plane, wherein the first plane is at an angle of rotation with respect to the second plane;
   d) wherein the first longitudinal axis of the first flange is laterally offset with respect to the second longitudinal axis of the second flange; and
   e) wherein at least one of the threaded holes in either the first flange or the second flange is an overlapping threaded hole comprising an upper portion extending from an oval shaped opening at either the top first flange surface or the top second flange surface part way through the respective first thickness or the second thickness to a threaded lower portion having an hourglass shape extending from where the upper portion ends at the hourglass shape to the bottom first flange surface or the bottom second flange surface with overlapping threaded surfaces of the overlapping threaded hole forming the hourglass shape, the threaded lower portion being adapted to lock with threads of a corresponding bone screw in either one or the other of the overlapping threaded surfaces of the at least one overlapping threaded hole.

2. The bone plate of claim 1 wherein the overlapping threaded hole is formed normal to at least one of the top first flange surface or the top second flange surface of the plate.

3. The bone plate of claim 1 wherein the overlapping threaded hole is formed at an angle offset from normal to at least one of the top first flange surface or the top second flange surface of the plate.

4. The bone plate of claim 1 wherein at least a first overlapping threaded hole is formed normal to at least one of the top first flange surface or the top second flange surface of the plate and at least a second overlapping threaded hole is formed at an angle offset from normal to at least one of the top first flange surface or the top second flange surface of the plate.

5. The bone plate of claims 1 wherein the at least one overlapping threaded hole further comprises sets of overlapping threaded holes.

6. The bone plate of claim 5 wherein the overlapping threaded holes are formed normal to at least one of the top first flange surface or the top second flange surface of the plate.

7. The bone plate of claim 5 wherein the overlapping threaded holes are formed at an angle offset from normal to at least one of the top first flange surface or the top second flange surface of the plate.

8. The bone plate of claim 1 wherein at least a first overlapping threaded hole is formed normal to at least one of the top first flange surface or the top second flange surface of the plate and at least a second overlapping threaded hole is formed at an angle offset from normal to at least one of the top first flange surface or the top second flange surface of the plate.

9. The bone plate of claim 5 wherein the sets of overlapping threaded holes are offset from either the first or the second longitudinal axis.

10. The bone plate of claim 5 wherein the sets of overlapping threaded holes are positioned in a staggered arrangement from either the first or the second longitudinal axis.

11. The bone plate of claim 5 wherein the sets of overlapping threaded holes are formed normal to at least one of the top first flange surface or the top second flange surface of the plate.

12. The bone plate of claim 5 wherein the sets of overlapping threaded holes are formed at an angle offset from normal to at least one of the top first flange surface or the top second flange surface of the plate.

13. The bone plate of claim 5 wherein at least a first set of overlapping threaded holes is formed normal to at least one of the top first flange surface or the top second flange surface of the plate and at least a second set of overlapping threaded holes is formed at an angle offset from normal to at least one of the top first flange surface or the top second flange surface of the plate.

14. The bone plate of claim 1 wherein the overlapping threaded hole is adapted to receive a bone screw with a head and a bone-engaging thread.

15. The bone plate of claim 14 wherein the head of the bone screw has a plate engaging thread.

16. The bone plate of claim 1 wherein the web provides the first plane of the first flange being at an angle of 20° with respect to the second plane of the second flange.

17. An orthopedic kit including:
   a) a bone plate comprising;
      i) a first flange lying in a first plane, the first flange having a first thickness extending from a top first flange surface to a bottom first flange surface with at least one threaded hole formed through the first thickness, wherein the first flange has a first longitudinal axis;
      ii) a second flange lying in a second plane, the second flange having a second thickness extending from a top second flange surface to a bottom second flange surface with at least one threaded hole formed through the second thickness, wherein the second flange has a second longitudinal axis;
      iii) a web connecting the first flange lying in the first plane to the second flange lying in the second plane, wherein the first plane is at an angle of rotation with respect to the second plane;
      iv) wherein the first longitudinal axis of the first flange is laterally offset with respect to the second longitudinal axis of the second flange; and
      v) wherein at least one of the threaded holes in either the first flange or the second flange is an overlapping threaded hole comprising an upper portion extending from an oval shaped opening at either the top first flange surface or the top second flange surface part way through the respective first thickness or the second thickness to a threaded lower portion having an hourglass shape extending from where the upper portion ends at the hourglass shape to the bottom first flange surface or the bottom second flange surface with overlapping threaded surfaces of the overlapping threaded hole forming the hourglass shape, the threaded lower portion being adapted to lock with threads of a corresponding bone screw in either one or the other of the overlapping threaded surfaces of the at least one overlapping threaded hole; and b) at least one bone screw engagable with the bone plate.

18. The kit of claim 17 further comprising a drill guide having a main drill guide surface and opposite end portions, one end portion of which is securely engagable with the overlapping threaded hole in the bone plate so as to securely hold the drill guide in a desired orientation with respect to the bone plate for stabilizing a drill used in an orthopedic procedure.

19. The bone plate of claim 17 wherein the web provides the first plane of the first flange being at an angle of 20° with respect to the second plane of the second flange.

20. A bone plate, comprising:
a) a first flange lying in a first plane, the first flange having a first thickness extending from a top first flange surface to a bottom first flange surface with at least one threaded hole formed through the first thickness, wherein the first flange has a first longitudinal axis;
b) a second flange lying in a second plane, the second flange having a second thickness extending from a top second flange surface to a bottom second flange surface with at least one threaded hole formed through the second thickness, wherein the second. flange has a second longitudinal axis;
c) a web connecting the first flange lying in the first plane to the second flange lying in the second plane, wherein the first plane is at an angle of rotation with respect to the second plane;
d) wherein the first longitudinal axis of the first flange is laterally offset with respect to the second longitudinal axis of the second flange; and
e) wherein at least one of the threaded holes in either the first flange or the second flange is an overlapping threaded hole comprising an upper portion extending from an oval shaped opening at either the top first flange surface or the top second flange surface part way through the respective first thickness or the second thickness to a threaded lower portion having an hourglass shape extending from where the upper portion ends at the hourglass shape to the bottom first flange surface or the bottom second flange surface with overlapping threaded surfaces of the overlapping threaded hole forming the hourglass shape, the threaded lower portion being adapted to lock with threads of a corresponding bone screw with a threaded head and a bone engaging threaded shank.

21. The bone plate of claim 20 wherein the web provides the first plane of the first flange being at an angle of 20° with respect to the second plane of the second flange.

22. A bone plate, comprising:
a) a first flange lying in a first plane, the first flange having a first thickness extending from a top first flange surface to a bottom first flange surface with at least one threaded hole formed through the first thickness, wherein the first flange has a first longitudinal axis;
b) a second flange lying in a second plane, the second flange having a second thickness extending from a top second flange surface to a bottom second flange surface with at least one threaded hole formed through the second thickness, wherein the second flange has a second longitudinal axis;
c) a web connecting the first flange lying in the first plane to the second flange lying in the second plane, wherein the first plane is at an angle of rotation with respect to the second plane;
d) wherein the first longitudinal axis of the first flange is laterally offset with respect to the second longitudinal axis of the second flange; and
e) wherein at least one of the threaded holes in either the first flange or the second flange is an overlapping threaded hole comprising an upper portion extending from an oval shaped opening at either the top first flange surface or the top second flange surface part way through the respective first thickness or the second thickness to a threaded lower portion having an hourglass shape extending from where the upper portion ends at the hourglass shape to the bottom first flange surface or the bottom second flange surface with overlapping threaded surfaces of the overlapping threaded hole forming the hourglass shape, the threaded lower portion being adapted to lock with bone screws having a threaded head and a bone engaging threaded shank, wherein the overlapping threaded surfaces of the at least one overlapping threaded hole have centers substantially aligned along either the first or the second longitudinal axis of the respective first and second flanges of the plate.

23. The bone plate of claim 22 wherein the web provides the first plane of the first flange being at an angle of 20° with respect to the second plane of the second flange.

24. A bone plate, comprising:
a) a first flange lying in a first plane, the first flange having a first thickness extending from a top first flange surface to a bottom first flange surface with at least one threaded hole formed through the first thickness, wherein the first flange has a first longitudinal axis;
b) a second flange lying in a second plane, the second flange having a second thickness extending from a top second flange surface to a bottom second flange surface with at least one threaded hole formed through the second thickness, wherein the second flange has a second longitudinal axis;
c) a web connecting the first flange lying in the first plane to the second flange lying in the second plane, wherein the first plane is at an angle of rotation with respect to the second plane;
d) wherein the first longitudinal axis of the first flange is laterally offset with respect to the second longitudinal axis of the second flange; and
e) wherein a plurality of threaded apertures communicate through both the first and second thicknesses of the respective first and second flanges of the plate, at least one of the threaded apertures in either the first or the second flange is comprised of an overlapping threaded hole comprising an upper portion extending from an oval shaped opening at either the top first flange surface or the top second flange surface part way through the respective first thickness or the second thickness to a threaded lower portion having an hourglass shape extending from where the upper portion ends at the hourglass shape to the bottom first flange surface or the bottom second flange surface with overlapping threaded surfaces of the overlapping threaded hole forming the hourglass shape, the threaded lower portion being adapted to lock with a bone screw with a head and a bone engaging thread, the overlapping threaded surfaces of the at least one overlapping threaded hole further having centers staggered about either the first or the second longitudinal axis of the respective first and second flanges of the plate.

25. The bone plate of claim 24 wherein the web provides the first plane of the first flange being at an angle of 20° with respect to the second plane of the second flange.

* * * * *